(12) United States Patent
Vitello et al.

(10) Patent No.: US 11,904,149 B1
(45) Date of Patent: Feb. 20, 2024

(54) ORAL TAMPER EVIDENT CLOSURE WITH RETAINED INDICATOR

(71) Applicants: Jonathan Vitello, Ft. Lauderdale, FL (US); Peter Lehel, Boca Raton, FL (US)

(72) Inventors: Jonathan Vitello, Ft. Lauderdale, FL (US); Peter Lehel, Boca Raton, FL (US)

(*) Notice: Subject to any disclaimer, the term of this patent is extended or adjusted under 35 U.S.C. 154(b) by 274 days.

(21) Appl. No.: 17/179,131

(22) Filed: Feb. 18, 2021

Related U.S. Application Data (60) Provisional application No. 62/978,121, filed on Feb. 18, 2020.

(51) Int. Cl.
*A61M 5/32* (2006.01)
*A61M 5/50* (2006.01)

(52) U.S. Cl.
CPC ........ *A61M 5/3202* (2013.01); *A61M 5/5086* (2013.01)

(58) Field of Classification Search
CPC .. A61M 5/3202; A61M 5/5086; A61M 39/20; A61M 39/1011; B65D 27/30; B65D 33/34; B65D 5/54; B65D 17/00; B65D 27/34; B65D 41/32; B65D 47/36; B65D 49/12; B65D 51/20; B65D 55/06
See application file for complete search history.

(56) References Cited

U.S. PATENT DOCUMENTS

| | | |
|---|---|---|
| 722,943 A | 3/1903 | Chappell |
| 732,662 A | 6/1903 | Smith |
| 3,489,268 A | 1/1970 | Meierhoefer |
| 3,574,306 A | 4/1971 | Alden |
| 3,674,181 A | 7/1972 | Marks et al. |
| 3,700,215 A | 10/1972 | Hardman et al. |
| 3,706,307 A | 12/1972 | Hasson |

(Continued)

FOREIGN PATENT DOCUMENTS

| | | |
|---|---|---|
| GB | 486367 | 6/1938 |
| JP | 08002544 | 1/1996 |

(Continued)

OTHER PUBLICATIONS

Arai Tsugio, Pilfering Proof Cap, Jan. 1, 1996.

*Primary Examiner* — Brandy S Lee
*Assistant Examiner* — Rachel T. Smith
(74) *Attorney, Agent, or Firm* — Malloy & Malloy, PL; Jennie S. Malloy (57) ABSTRACT

A closure assembly for a syringe or other medical administering device includes an outer sleeve having an access opening and a tip cap removably disposed therein. The tip cap includes a flow restrictor structured for removable, flow restricting connection to the syringe. An indicator member is removably connected within the outer sleeve, in interruptive relation to passage of the tip cap through the access opening. A retaining structure is fixedly connected to the flow restrictor and movable therewith relative to the indicator member. The retaining structure and flow restrictor are collectively structured for retaining engagement of the tip cap with the indicator member, as the tip and indicator member are concurrently removed from the outer sleeve and as the tip cap is disconnected from the flow restricting connection with the syringe.

12 Claims, 3 Drawing Sheets

(56) References Cited

U.S. PATENT DOCUMENTS

| | | |
|---|---|---|
| 3,712,749 A | 1/1973 | Roberts |
| 3,726,445 A | 4/1973 | Ostrowsky et al. |
| 3,747,751 A | 7/1973 | Miller et al. |
| 3,850,329 A | 11/1974 | Robinson |
| 3,872,867 A | 3/1975 | Killinger |
| 3,904,033 A | 9/1975 | Haerr |
| 3,905,375 A | 9/1975 | Toyama |
| 3,937,211 A | 2/1976 | Merten |
| 3,987,930 A | 10/1976 | Fuson |
| 4,005,739 A | 2/1977 | Winchell |
| 4,043,334 A | 8/1977 | Brown et al. |
| 4,046,145 A | 9/1977 | Choksi et al. |
| 4,068,696 A | 1/1978 | Winchell |
| 4,106,621 A | 8/1978 | Sorenson |
| 4,216,585 A | 8/1980 | Hatter |
| 4,216,872 A | 8/1980 | Bean |
| 4,244,366 A | 1/1981 | Raines |
| 4,252,122 A | 2/1981 | Halvorsen |
| 4,271,972 A | 6/1981 | Thor |
| 4,286,591 A | 9/1981 | Raines |
| 4,286,640 A | 9/1981 | Knox et al. |
| 4,313,539 A | 2/1982 | Raines |
| 4,369,781 A | 1/1983 | Gilson et al. |
| 4,420,085 A | 12/1983 | Wilson et al. |
| 4,430,077 A | 2/1984 | Mittleman et al. |
| 4,457,445 A | 7/1984 | Hanks et al. |
| 4,482,071 A | 11/1984 | Ishiwatari |
| D277,783 S | 2/1985 | Beck |
| 4,521,237 A | 6/1985 | Logothetis |
| 4,530,697 A | 7/1985 | Kuhlemann et al. |
| 4,571,242 A | 2/1986 | Klien et al. |
| 4,589,171 A | 5/1986 | McGill |
| 4,664,259 A | 5/1987 | Landis |
| 4,667,837 A | 5/1987 | Vitello et al. |
| 4,676,530 A | 6/1987 | Nordgren et al. |
| 4,693,707 A | 9/1987 | Dye |
| 4,726,483 A | 2/1988 | Drozd |
| 4,735,617 A | 4/1988 | Nelson et al. |
| 4,742,910 A | 5/1988 | Staebler |
| 4,743,229 A | 5/1988 | Chu |
| 4,743,231 A | 5/1988 | Kay et al. |
| 4,760,847 A | 8/1988 | Vaillancourt |
| 4,813,564 A | 3/1989 | Cooper et al. |
| 4,832,695 A | 5/1989 | Rosenberg et al. |
| 4,834,706 A | 5/1989 | Beck et al. |
| 4,842,592 A | 6/1989 | Caggiani et al. |
| 4,844,906 A | 7/1989 | Hermelin et al. |
| 4,906,231 A | 3/1990 | Young |
| 4,919,285 A | 4/1990 | Roof et al. |
| 4,936,445 A | 6/1990 | Grabenkort |
| 5,009,323 A | 4/1991 | Montgomery et al. |
| 5,024,323 A | 6/1991 | Bolton |
| 5,049,129 A | 9/1991 | Zdeb et al. |
| D323,392 S | 1/1992 | Bryne |
| 5,078,696 A | 1/1992 | Nedbaluk |
| 5,085,332 A | 2/1992 | Gettig et al. |
| 5,090,564 A | 2/1992 | Chimienti |
| 5,133,454 A | 7/1992 | Hammer |
| 5,135,496 A | 8/1992 | Vetter et al. |
| 5,163,922 A | 11/1992 | McElveen, Jr. et al. |
| 5,165,560 A | 11/1992 | Ennis, III et al. |
| 5,230,429 A | 7/1993 | Etheredge, III |
| 5,267,983 A | 12/1993 | Oilschlager et al. |
| 5,292,308 A | 3/1994 | Ryan |
| 5,293,993 A | 3/1994 | Yates, Jr. et al. |
| 5,295,599 A | 3/1994 | Smith |
| 5,312,367 A | 5/1994 | Nathan |
| 5,312,368 A | 5/1994 | Haynes |
| 5,328,466 A | 7/1994 | Denmark |
| 5,328,474 A | 7/1994 | Raines |
| 5,356,380 A | 10/1994 | Hoekwater et al. |
| 5,370,226 A | 12/1994 | Gollobin et al. |
| 5,380,295 A | 1/1995 | Vacca |
| 5,402,887 A | 4/1995 | Shillington |
| 5,405,339 A | 4/1995 | Kohnen et al. |
| 5,456,668 A | 10/1995 | Ogle, II |
| 5,458,580 A | 10/1995 | Hajishoreh |
| 5,468,224 A | 11/1995 | Souryal |
| 5,474,178 A | 12/1995 | DiViesti et al. |
| 5,505,705 A | 4/1996 | Galpin et al. |
| 5,531,695 A | 7/1996 | Swisher |
| 5,540,666 A | 7/1996 | Barta et al. |
| 5,549,571 A | 8/1996 | Sak |
| 5,558,648 A | 9/1996 | Shields |
| 5,584,817 A | 12/1996 | van den Haak |
| 5,588,239 A | 12/1996 | Anderson |
| 5,617,954 A | 4/1997 | Kato et al. |
| 5,624,402 A | 4/1997 | Imbert |
| 5,662,233 A | 9/1997 | Reid |
| 5,674,209 A | 10/1997 | Yarger |
| 5,695,470 A | 12/1997 | Roussigne et al. |
| 5,700,247 A | 12/1997 | Grimard et al. |
| 5,702,374 A | 12/1997 | Johnson |
| 5,713,485 A | 2/1998 | Liff et al. |
| 5,776,124 A | 7/1998 | Wald |
| 5,785,691 A | 7/1998 | Vetter et al. |
| 5,797,885 A | 8/1998 | Rubin |
| 5,807,343 A | 9/1998 | Tucker et al. |
| 5,829,589 A | 11/1998 | Nguyen et al. |
| D402,768 S | 12/1998 | Smith et al. |
| 5,842,567 A | 12/1998 | Rowe et al. |
| 5,876,381 A | 3/1999 | Pond et al. |
| 5,883,806 A | 3/1999 | Meador et al. |
| 5,884,457 A | 3/1999 | Ortiz et al. |
| 5,902,269 A | 5/1999 | Jentzen |
| 5,926,922 A | 7/1999 | Stottle |
| 5,951,522 A | 9/1999 | Rosato et al. |
| 5,951,525 A | 9/1999 | Thorne et al. |
| 5,954,657 A | 9/1999 | Rados |
| 5,957,166 A | 9/1999 | Safabash |
| 5,957,314 A | 9/1999 | Nishida et al. |
| 5,963,136 A | 10/1999 | O'Brien |
| 5,989,227 A | 11/1999 | Vetter et al. |
| 5,993,437 A | 11/1999 | Raoz |
| 6,000,548 A | 12/1999 | Tsals |
| D419,671 S | 1/2000 | Jansen |
| 6,021,824 A | 2/2000 | Larsen et al. |
| 6,027,482 A | 2/2000 | Imbert |
| 6,068,614 A | 5/2000 | Kimber et al. |
| D430,293 S | 8/2000 | Jansen |
| D431,864 S | 10/2000 | Jansen |
| 6,126,640 A | 10/2000 | Tucker et al. |
| 6,190,364 B1 | 2/2001 | Imbert |
| 6,193,688 B1 | 2/2001 | Balestracci et al. |
| 6,196,593 B1 | 3/2001 | Petrick et al. |
| 6,196,998 B1 | 3/2001 | Jansen et al. |
| 6,216,885 B1 | 4/2001 | Guillaume |
| 6,279,746 B1 | 4/2001 | Hussaini et al. |
| 6,235,376 B1 | 5/2001 | Miyazaki et al. |
| 6,280,418 B1 | 8/2001 | Reinhard et al. |
| 6,287,671 B1 | 9/2001 | Bright et al. |
| 6,322,543 B1 | 11/2001 | Singh et al. |
| 6,338,200 B1 | 1/2002 | Baxa et al. |
| 6,358,241 B1 | 3/2002 | Shapeton et al. |
| 6,375,640 B1 | 4/2002 | Teraoka |
| 6,394,983 B1 | 5/2002 | Mayoral et al. |
| 6,439,276 B1 | 8/2002 | Wood et al. |
| 6,485,460 B2 | 11/2002 | Eakins et al. |
| 6,488,666 B1 | 12/2002 | Geist |
| 6,491,665 B1 | 12/2002 | Vetter et al. |
| 6,500,155 B2 | 12/2002 | Sasso |
| 6,520,935 B1 | 2/2003 | Jansen et al. |
| 6,540,697 B2 | 4/2003 | Chen |
| 6,565,529 B1 | 5/2003 | Kimber et al. |
| 6,581,792 B1 | 6/2003 | Limanjaya |
| 6,585,691 B1 | 7/2003 | Vitello |
| 6,592,251 B2 | 7/2003 | Edwards et al. |
| 6,666,852 B2 | 12/2003 | Niedospial, Jr. |
| 6,682,798 B1 | 1/2004 | Kiraly |
| 6,726,652 B2 | 4/2004 | Eakins et al. |
| 6,726,672 B1 | 4/2004 | Hanly et al. |
| 6,764,469 B2 | 7/2004 | Broselow |
| 6,796,586 B2 | 9/2004 | Werth |
| 6,821,268 B2 | 11/2004 | Balestracci |

(56) References Cited

U.S. PATENT DOCUMENTS

| | | |
|---|---|---|
| D501,549 S | 2/2005 | McAllister et al. |
| 6,921,383 B2 | 7/2005 | Vitello |
| 6,935,560 B2 | 8/2005 | Andreasson et al. |
| 6,942,643 B2 | 9/2005 | Eakins et al. |
| 7,036,661 B2 | 5/2006 | Anthony et al. |
| 7,055,273 B2 | 6/2006 | Roshkoff |
| 7,100,771 B2 | 9/2006 | Massengale et al. |
| 7,125,397 B2 | 10/2006 | Woehr et al. |
| 7,141,286 B1 | 11/2006 | Kessler et al. |
| 7,175,081 B2 | 2/2007 | Andreasson et al. |
| 7,182,256 B2 | 2/2007 | Andreasson et al. |
| 7,232,066 B2 | 6/2007 | Anderasson et al. |
| 7,240,926 B2 | 7/2007 | Dalle et al. |
| 7,299,981 B2 | 11/2007 | Hickle et al. |
| 7,374,555 B2 | 5/2008 | Heinz et al. |
| 7,404,500 B2 | 7/2008 | Marteau et al. |
| 7,410,803 B2 | 8/2008 | Nollert et al. |
| 7,425,208 B1 | 9/2008 | Vitello |
| 7,437,972 B2 | 10/2008 | Yeager |
| D581,046 S | 11/2008 | Sudo |
| D581,047 S | 11/2008 | Koshidaka |
| D581,049 S | 11/2008 | Sudo |
| 7,482,166 B2 | 1/2009 | Nollert et al. |
| D589,612 S | 3/2009 | Sudo |
| 7,497,330 B2 | 3/2009 | Anthony et al. |
| 7,503,453 B2 | 3/2009 | Cronin et al. |
| 7,588,563 B2 | 9/2009 | Guala |
| 7,594,681 B2 | 9/2009 | DeCarlo |
| 7,608,057 B2 | 10/2009 | Woehr et al. |
| 7,611,487 B2 | 11/2009 | Woehr et al. |
| 7,632,244 B2 | 12/2009 | Buehler et al. |
| D608,900 S | 1/2010 | Giraud et al. |
| 7,641,636 B2 | 1/2010 | Moesli et al. |
| D612,939 S | 3/2010 | Boone, III et al. |
| 7,681,606 B2 | 3/2010 | Khan et al. |
| 7,698,180 B2 | 4/2010 | Fago et al. |
| 7,735,664 B1 | 6/2010 | Peters et al. |
| 7,748,892 B2 | 7/2010 | McCoy |
| 7,762,988 B1 | 7/2010 | Vitello |
| 7,766,919 B2 | 8/2010 | Delmotte |
| 7,802,313 B2 | 9/2010 | Czajka |
| 7,886,908 B2 | 2/2011 | Farrar et al. |
| 7,918,830 B2 | 4/2011 | Langan et al. |
| 7,922,213 B2 | 4/2011 | Werth |
| 8,034,041 B2 | 10/2011 | Domkowski et al. |
| 8,079,518 B2 | 12/2011 | Turner et al. |
| 8,091,727 B2 | 1/2012 | Domkowwski |
| 8,118,788 B2 | 2/2012 | Frezza |
| 8,137,324 B2 | 3/2012 | Bobst |
| 8,140,349 B2 | 3/2012 | Hanson et al. |
| 8,252,247 B2 | 8/2012 | Ferlic |
| 8,257,286 B2 | 9/2012 | Meyer et al. |
| 8,328,082 B1 | 12/2012 | Bochenko et al. |
| 8,348,895 B1 | 1/2013 | Vitello |
| 8,353,869 B2 | 1/2013 | Ranalletta et al. |
| 8,413,811 B1 | 4/2013 | Arendt |
| 8,443,999 B1 | 5/2013 | Reinders |
| D684,057 S | 6/2013 | Kwon |
| 8,512,277 B2 | 8/2013 | Del Vecchio |
| 8,528,757 B2 | 9/2013 | Bisio |
| 8,556,074 B2 | 10/2013 | Turner et al. |
| 8,579,116 B2 | 11/2013 | Pether et al. |
| 8,591,462 B1 | 11/2013 | Vitello |
| 8,597,255 B2 | 12/2013 | Emmott et al. |
| 8,597,271 B2 | 12/2013 | Langan et al. |
| 8,616,413 B2 | 12/2013 | Koyama |
| D701,304 S | 3/2014 | Lair et al. |
| 8,672,902 B2 | 3/2014 | Ruan et al. |
| 8,702,674 B2 | 4/2014 | Bochenko |
| 8,777,910 B2 | 7/2014 | Bauss et al. |
| 8,777,930 B2 | 7/2014 | Swisher et al. |
| 8,852,561 B2 | 10/2014 | Wagner et al. |
| 8,864,021 B1 | 10/2014 | Vitello |
| 8,864,707 B1 | 10/2014 | Vitello |
| 8,864,708 B1 | 10/2014 | Vitello |
| 8,911,424 B2 | 12/2014 | Weadock et al. |
| 8,945,082 B2 | 2/2015 | Geiger et al. |
| 9,016,473 B2 | 4/2015 | Tamarindo |
| 9,082,157 B2 | 7/2015 | Gibson |
| 9,101,534 B2 | 8/2015 | Bochenko |
| D738,495 S | 9/2015 | Strong et al. |
| 9,125,976 B2 | 9/2015 | Uber, III et al. |
| D743,019 S | 11/2015 | Schultz |
| 9,199,042 B2 | 12/2015 | Farrar et al. |
| 9,199,749 B1 | 12/2015 | Vitello et al. |
| 9,220,486 B2 | 12/2015 | Schweiss et al. |
| 9,220,577 B2 | 12/2015 | Jessop et al. |
| D750,228 S | 2/2016 | Strong et al. |
| 9,272,099 B2 | 3/2016 | Limaye et al. |
| 9,311,592 B1 | 4/2016 | Vitello et al. |
| D756,777 S | 5/2016 | Berge et al. |
| 9,336,669 B2 | 5/2016 | Bowden et al. |
| D759,488 S | 6/2016 | Ingram et al. |
| D760,384 S | 6/2016 | Niunoya et al. |
| D760,902 S | 7/2016 | Persson |
| 9,402,967 B1 | 8/2016 | Vitello |
| 9,427,715 B2 | 8/2016 | Palazzolo et al. |
| 9,433,768 B2 | 9/2016 | Tekeste et al. |
| 9,463,310 B1 | 10/2016 | Vitello |
| D773,043 S | 11/2016 | Ingram et al. |
| D777,903 S | 1/2017 | Schultz |
| 9,662,456 B2 | 5/2017 | Woehr |
| D789,529 S | 6/2017 | Davis et al. |
| 9,687,249 B2 | 6/2017 | Hanlon et al. |
| 9,744,304 B2 | 8/2017 | Swift et al. |
| D797,928 S | 9/2017 | Davis et al. |
| D797,929 S | 9/2017 | Davis et al. |
| 9,764,098 B2 | 9/2017 | Hund et al. |
| 9,821,152 B1 | 11/2017 | Vitello et al. |
| D806,241 S | 12/2017 | Swinney et al. |
| D807,503 S | 1/2018 | Davis et al. |
| 9,855,191 B1 | 1/2018 | Vitello et al. |
| D815,945 S | 4/2018 | Fischer |
| 9,987,438 B2 | 6/2018 | Stillson |
| D825,746 S | 8/2018 | Davis et al. |
| 10,039,913 B2 | 8/2018 | Yeh et al. |
| D831,201 S | 10/2018 | Holtz et al. |
| D834,187 S | 11/2018 | Ryan |
| 10,124,122 B2 | 11/2018 | Zenker |
| 10,166,343 B1 | 1/2019 | Hunt et al. |
| 10,166,347 B1 | 1/2019 | Vitello |
| 10,183,129 B1 | 1/2019 | Vitello |
| 10,207,099 B1 | 2/2019 | Vitello |
| D842,484 S | 3/2019 | Davis et al. |
| D847,373 S | 4/2019 | Hurwit et al. |
| 10,300,263 B1 | 5/2019 | Hunt |
| 10,307,548 B1 | 6/2019 | Hunt et al. |
| 10,315,024 B1 | 6/2019 | Vitello et al. |
| 10,315,808 B2 | 6/2019 | Taylor et al. |
| 10,376,655 B2 | 8/2019 | Pupke et al. |
| D859,125 S | 9/2019 | Weagle et al. |
| 10,478,262 B2 | 11/2019 | Niese et al. |
| 10,758,684 B1 | 9/2020 | Vitello et al. |
| 10,773,067 B2 | 9/2020 | Davis et al. |
| 10,888,672 B1 | 1/2021 | Vitello |
| 10,898,659 B1 | 1/2021 | Vitello et al. |
| 10,912,898 B1 | 2/2021 | Vitello et al. |
| 10,933,202 B1 | 3/2021 | Banik |
| 10,953,162 B1 | 3/2021 | Hunt et al. |
| 11,097,071 B1 | 8/2021 | Hunt et al. |
| 11,278,681 B1 | 3/2022 | Banik et al. |
| D948,713 S | 4/2022 | Banik |
| 11,357,588 B1 | 6/2022 | Vitello et al. |
| 11,413,406 B1 | 8/2022 | Vitello et al. |
| 11,426,328 B1 | 8/2022 | Ollmann et al. |
| 11,471,610 B1 | 10/2022 | Banik et al. |
| 11,523,970 B1 | 12/2022 | Vitello et al. |
| 11,541,180 B1 | 1/2023 | Vitello et al. |
| 11,690,994 B1 | 7/2023 | Banik et al. |
| 11,697,527 B1 | 7/2023 | Hendren et al. |
| 11,779,520 B1 | 10/2023 | Vitello |
| 11,793,987 B1 | 10/2023 | Vitello et al. |
| 2001/0056258 A1 | 12/2001 | Evans |
| 2002/0023409 A1 | 2/2002 | Py |

(56) References Cited

U.S. PATENT DOCUMENTS

| | | |
|---|---|---|
| 2002/0046962 A1 | 4/2002 | Vallans et al. |
| 2002/0079281 A1 | 6/2002 | Hierzer et al. |
| 2002/0097396 A1 | 7/2002 | Schafer |
| 2002/0099334 A1 | 7/2002 | Hanson et al. |
| 2002/0101656 A1 | 8/2002 | Blumenthal et al. |
| 2002/0104770 A1 | 8/2002 | Shapeton et al. |
| 2002/0133119 A1 | 9/2002 | Eakins et al. |
| 2003/0055885 A1 | 3/2003 | Cobb et al. |
| 2003/0146617 A1 | 8/2003 | Franko, Sr. |
| 2003/0183547 A1 | 10/2003 | Heyman |
| 2003/0187403 A1 | 10/2003 | Balestracci |
| 2004/0008123 A1 | 1/2004 | Carrender et al. |
| 2004/0064095 A1 | 4/2004 | Vitello |
| 2004/0116858 A1 | 6/2004 | Heinz et al. |
| 2004/0173563 A1 | 9/2004 | Kim et al. |
| 2004/0186437 A1 | 9/2004 | Frenette et al. |
| 2004/0225258 A1 | 11/2004 | Balestracci |
| 2005/0146081 A1 | 7/2005 | MacLean et al. |
| 2005/0148941 A1 | 7/2005 | Farrar et al. |
| 2005/0209555 A1 | 9/2005 | Middleton et al. |
| 2006/0084925 A1 | 4/2006 | Ramsahoye |
| 2006/0089601 A1 | 4/2006 | Dionigi |
| 2006/0169611 A1 | 8/2006 | Prindle |
| 2006/0173415 A1 | 8/2006 | Cummins |
| 2006/0189933 A1 | 8/2006 | Alheidt et al. |
| 2007/0060898 A1 | 3/2007 | Shaughnessy et al. |
| 2007/0106234 A1 | 5/2007 | Klein |
| 2007/0142786 A1 | 6/2007 | Lampropoulos et al. |
| 2007/0191890 A1 | 8/2007 | Hasse et al. |
| 2007/0219503 A1 | 9/2007 | Loop et al. |
| 2007/0257111 A1 | 11/2007 | Ortenzi |
| 2008/0068178 A1 | 3/2008 | Meyer |
| 2008/0097310 A1 | 4/2008 | Buchler et al. |
| 2008/0106388 A1 | 5/2008 | Knight |
| 2008/0140020 A1 | 6/2008 | Shirley |
| 2008/0243088 A1 | 10/2008 | Evans |
| 2008/0303267 A1 | 12/2008 | Schnell et al. |
| 2008/0306443 A1 | 12/2008 | Neer |
| 2009/0084804 A1 | 4/2009 | Caspary et al. |
| 2009/0099552 A1 | 4/2009 | Levy et al. |
| 2009/0149815 A1 | 6/2009 | Kiel et al. |
| 2009/0166311 A1 | 7/2009 | Claessens |
| 2009/0326481 A1 | 12/2009 | Swisher et al. |
| 2010/0050351 A1 | 3/2010 | Colantonio et al. |
| 2010/0084403 A1 | 4/2010 | Popish et al. |
| 2010/0126894 A1 | 5/2010 | Koukol et al. |
| 2010/0179822 A1 | 7/2010 | Reppas |
| 2010/0228226 A1 | 9/2010 | Nielsen |
| 2010/0252564 A1 | 10/2010 | Martinez et al. |
| 2010/0283238 A1 | 11/2010 | Deighan et al. |
| 2011/0044850 A1 | 2/2011 | Solomon et al. |
| 2011/0046550 A1 | 2/2011 | Schiller et al. |
| 2011/0046603 A1 | 2/2011 | Felsovalyi et al. |
| 2012/0064515 A2 | 3/2012 | Knapp et al. |
| 2012/0096957 A1 | 4/2012 | Ochman |
| 2012/0110950 A1 | 5/2012 | Schraudolph |
| 2013/0018356 A1 | 1/2013 | Prince et al. |
| 2013/0056130 A1 | 3/2013 | Alpert et al. |
| 2013/0088354 A1 | 4/2013 | Thomas |
| 2013/0237949 A1 | 9/2013 | Miller |
| 2013/0269592 A1 | 10/2013 | Heacock et al. |
| 2014/0000781 A1 | 1/2014 | Franko, Jr. |
| 2014/0034536 A1 | 2/2014 | Reinhardt et al. |
| 2014/0069202 A1 | 3/2014 | Fisk |
| 2014/0069829 A1 | 3/2014 | Evans |
| 2014/0076840 A1 | 3/2014 | Graux et al. |
| 2014/0135738 A1 | 5/2014 | Panian |
| 2014/0155888 A1 | 6/2014 | Nelson et al. |
| 2014/0163465 A1 | 6/2014 | Bartlett et al. |
| 2014/0257843 A1 | 9/2014 | Adler et al. |
| 2014/0326727 A1 | 11/2014 | Jouin et al. |
| 2014/0353196 A1 | 12/2014 | Key |
| 2015/0013811 A1 | 1/2015 | Carrel et al. |
| 2015/0048045 A1 | 2/2015 | Miceli et al. |
| 2015/0112296 A1 | 4/2015 | Ishiwata et al. |
| 2015/0136632 A1 | 5/2015 | Moir et al. |
| 2015/0182886 A1 | 7/2015 | Okihara |
| 2015/0191633 A1 | 7/2015 | De Boer et al. |
| 2015/0246185 A1 | 9/2015 | Heinz |
| 2015/0302232 A1 | 10/2015 | Strassburger et al. |
| 2015/0305982 A1 | 10/2015 | Bochenko |
| 2015/0310771 A1 | 10/2015 | Atkinson et al. |
| 2016/0067144 A1 | 3/2016 | Chang |
| 2016/0067422 A1 | 3/2016 | Davis et al. |
| 2016/0090456 A1 | 3/2016 | Ishimaru et al. |
| 2016/0136352 A1 | 5/2016 | Smith et al. |
| 2016/0144119 A1 | 5/2016 | Limaye et al. |
| 2016/0158110 A1 | 6/2016 | Swisher et al. |
| 2016/0158449 A1 | 6/2016 | Limaye et al. |
| 2016/0176550 A1 | 6/2016 | Viitello et al. |
| 2016/0194121 A1 | 7/2016 | Ogawa et al. |
| 2016/0250420 A1 | 9/2016 | Maritan et al. |
| 2016/0279032 A1 | 9/2016 | Davis et al. |
| 2016/0328586 A1 | 11/2016 | Bowden et al. |
| 2016/0361235 A1 | 12/2016 | Swisher |
| 2016/0367439 A1 | 12/2016 | Davis et al. |
| 2017/0007771 A1 | 1/2017 | Duinat et al. |
| 2017/0014310 A1 | 1/2017 | Hyun et al. |
| 2017/0124289 A1 | 5/2017 | Hasan et al. |
| 2017/0173321 A1 | 6/2017 | Davis et al. |
| 2017/0203086 A1 | 7/2017 | Davis |
| 2017/0225843 A1 | 8/2017 | Glaser et al. |
| 2017/0239141 A1 | 8/2017 | Davis et al. |
| 2017/0297781 A1 | 10/2017 | Kawamura |
| 2017/0319438 A1 | 11/2017 | Davis et al. |
| 2017/0354792 A1* | 12/2017 | Ward .................. A61M 5/3202 |
| 2018/0001540 A1 | 1/2018 | Byun |
| 2018/0014998 A1 | 1/2018 | Yuki et al. |
| 2018/0064604 A1 | 3/2018 | Drmanovic |
| 2018/0078684 A1 | 3/2018 | Peng et al. |
| 2018/0089593 A1 | 3/2018 | Patel et al. |
| 2018/0098915 A1 | 4/2018 | Rajagopal et al. |
| 2018/0147115 A1 | 5/2018 | Nishioka et al. |
| 2018/0312305 A1 | 11/2018 | Rognard |
| 2019/0308006 A1 | 10/2019 | Erekovcanski et al. |
| 2019/0388626 A1 | 12/2019 | Okihara |
| 2022/0008645 A1 | 1/2022 | Ukai et al. |

FOREIGN PATENT DOCUMENTS

| | | |
|---|---|---|
| WO | WO2008000279 | 1/2008 |
| WO | WO2017086607 | 5/2015 |

* cited by examiner

FIG. 6

ORAL TAMPER EVIDENT CLOSURE WITH RETAINED INDICATOR

This patent application claims priority to U.S. Provisional patent application, namely, that having Ser. No. 62/978,121 and a filing date of Feb. 18, 2020, the contents of which is incorporated herein by reference in its entirety.

BACKGROUND OF THE INVENTION

Field of the Invention

The present invention is directed to a closure for a medical administering device including, but not limited to, a prefilled oral syringe, comprising an outer sleeve containing a tip cap and an indicator member. The tip cap and the indicator member are cooperatively structured to establish a retaining engagement therebetween, which serves to retain the indicator member on the tip cap, concurrent to removal of the tip cap from the outer sleeve, and subsequent detachment of the tip cap from its flow restricting engagement with the syringe.

Description of the Related Art

In the medical field, it is a common procedure for authorized medical personnel to order medicine or other substances to be administered to a patient whether orally, by an injection or intravenously through an IV. It is also a relatively common procedure for a number of administering devices, such as a syringe, to be pre-filled by authorized personnel whether within the hospital or at another filling station. However, such a filling station is typically located in a remote part of the facility, relative to the patient care area, where the injection is to be administered. Because of the remote location of many nurses' stations, relative to a filling station, a fluid or drug loaded syringe or other medical device is frequently given to another person for delivery to a nurse's station for subsequent dosing of the patient. In the case where a prefilled drug in the syringe is very expensive or addictive such as, but not limited to, morphine, there is a danger of tampering, by a person seeking unauthorized access to the prefilled contents of the syringe or medical device.

If tampering does occur, the potential for serious consequences exists. For example, there is a possibility that the prescribed medicine will be replaced by some other, unauthorized substance. As an illustration of this, if saline solution were substituted for a dose of morphine or other medication, the result could be harmful to a patient. Thus, there is a problem of knowing if a sealed, pre-loaded syringe or other administering device has, or has not, been compromised by tampering and/or exposed to contamination so that it is no longer sterile.

In addition to the administration of drugs, medicine, etc., meaningful protection is required in the use of enteral feeding sets. As commonly recognized in the medical and related professions, the term "enteral" relates to the administration or removal of fluid to or from the gastrointestinal tract. Moreover, enteral connectors and/or fixtures of the type referred to herein relate to medical devices or accessories which are intended for use in enteral applications. Further, small-bore connectors for enteral applications may be employed for delivery of enteral nutrition fluid from a fluid source to the patient. Additionally, it is pointed out that enteral feeding sets and extension sets may include a female fixture, wherein the source of fluid flows to the patient initially through the female fixture and to and through a cooperatively structured male enteral fixture.

Therefore, regardless of the known or conventional attempts to provide a flow restricting closure to protect the contents of preloaded medical dispensers or administering devices, including oral syringes, certain problems still remain in this field of art. Accordingly, there is still a need for an improved, closure assembly which provides a secure and reliable, flow restricting and/or fluid sealing connection to the discharge port, fixture or connector of a medical device of the type set forth herein. If any such improved closure assembly were developed, it would preferably also overcome known disadvantages in the production and/or assembly of conventional closures, including tamper evident closures.

Known or prior art closures structured for connection in flow restricting relation to a medical administering device such as, but not limited to a syringe, commonly demonstrate tamper evident capabilities by including an indicating structure, which when exposed or otherwise positioned, provides a visual or other indication of tampering or use. By way of a nonlimiting example, known closures may be specifically structured for flow restricting connection to an oral syringe. In addition, authorized access to the contents of the oral syringe requires removal of at least a portion of the flow restricting closure assembly, which in turn may expose an indicating structure, of the type generally set forth above. When used, an individual must first remove a "tip cap" or like flow restricting structure associated with the closure and subsequently remove the indicator member from its position on the oral syringe, adjacent the discharge port thereof. Accordingly, there is some concern that a failure to subsequently remove the indicating structure from the syringe could potentially result in it being inadvertently delivered into the mouth of the patient or otherwise. As such, the separate removal of the tip cap and subsequently, removal of the indicating structure as well, cause an inconvenience to the authorized user, as well as potential danger to the patient.

In order to reduce, if not eliminate, the problems of the type set forth above, there is a need in the medical closure industry for a closure assembly having a sufficiently unique construction to avoid the required separate, independent removal of a flow restricting tip cap and also, an indicating structure, from an oral syringe or other medical administering device. Therefore, if any such improved closure assembly were developed, it would preferably include cooperatively dimensioned and structured components which facilitate the visual exposure of an indicating structure, such that use or tampering thereof and/or with the administering device is evident. However, such cooperative structural features of the closure components would preferably also be operative to provide for the concurrent removal of a tip cap or other flow restricting member, and any indicating structure from the discharge port of the syringe. In turn, any such improved device should help to overcome the above noted problems and eliminate the necessity of separate removal of the tip cap and indicating structure.

Finally, if any such improved closure assembly were developed, it should also be structurally and operatively reliable, while improving the cost effectiveness associated with the manufacture and assembly thereof.

SUMMARY OF THE INVENTION

The present invention is directed to a closure assembly for a medical administering device including, but not limited to, a prefilled oral syringe. As set forth in greater detail hereinafter, the closure assembly includes tamper evident capabilities and is structured to restrict unauthorized access to and removal of the contents of the oral syringe or other medical administering device.

In more specific terms, the closure assembly of the present invention comprises an outer sleeve including an access opening preferably, but not necessarily, defined by one open end of the outer sleeve. In cooperation therewith, the opposite end of the outer sleeve may be closed to further restrict access to the interior of the outer sleeve. The flow restricting capabilities of the closure assembly include the provision of a tip cap movably disposed on the interior of the outer sleeve in aligned and/or accessible relation to the access opening.

The aforementioned tamper evident capabilities include the provision of an indicator member removably connected to and disposed within the interior of the outer sleeve, between the access opening and the disposition of the tip cap, or lower end thereof within the outer sleeve. As such, the indicator member is disposed in interruptive relation to passage of the tip cap through the access opening, such as when it is connected to a discharge port of the syringe or other medical administering device. In at least one embodiment, the indicator member may be in the form of a ring or otherwise include a substantially annular configuration having an open interior. Removable attachment of the indicator member is accomplished by at least one, but more practically, a plurality of frangible members interconnecting the exterior of the indicator member to the interior surface of the outer sleeve. As a result, interruptive engagement of the indicator member with the tip cap, upon an attempted removal of the tip cap and connected syringe from within the outer sleeve, will result in a breakage of the one or more frangible members, and allow removal of the indicator member, with the tip cap mounted thereon, through the access opening. Further, the cooperative dimensions and structures of the indicator member, frangible members and interior surface of the outer sleeve prevents fixed reattachment of the indicator member on the interior of the outer sleeve.

As also explained in greater detail hereinafter, portions of the tip cap are cooperatively disposed, dimensioned and structured with the indicator member to establish a retaining engagement of the indicator member on the tip cap, concurrent to the removal of the tip cap from the outer sleeve, while the tip cap is connected to the syringe. Such attachment between the tip cap and the syringe comprises a flow restricting connection of a flow restrictor member associated with the tip cap, with a discharge port of the syringe. Such flow restricting engagement facilitates restricted access to the contents of the syringe, while the indicator member is mounted and/or disposed in retained engagement on the tip cap. The retention of the indicator member on or as part of the tip cap, so that they are concurrently removed from the interior on the outer sleeve, at least partially defines the aforementioned tamper evident capabilities, by visually indicating detachment of the indicator member from the interior of the outer sleeve.

As originally assembled, the tip cap is disposed within the interior of the outer sleeve, with an upper portion including a flow restrictor, disposed above the indicator member and the aforementioned closed end of the outer sleeve. In such a position, the tip cap is removably retained within the outer sleeve due to the removable attachment of the indicator member to the interior surface of the outer sleeve. Because the indicator member cannot be re-attached to the interior surface of the outer sleeve, attempts to reposition the outer sleeve in enclosing, retaining relation to the tip cap will be prevented.

The aforementioned retaining engagement between the tip cap and the indicator member may be considered a fixed attachment, although in at least one embodiment this may be a removably fixed attachment, and in at least one other embodiment of the present invention, it may be defined by a frictional, interference fit therebetween. Further, as defined herein the retaining engagement of the indicator member on the tip cap is maintained when the tip cap is removed from the discharge port of the syringe. As a result, when the syringe is prepared for use in administering the contents thereof to a patient, a user of the syringe will not be required to first remove the tip cap and thereafter, to separately remove the indicator member from the syringe, as is frequently required with known or prior art closure assemblies. This is due to the fact that the retaining engagement of the indicator member on the tip cap, as defined herein, is maintained as the tip cap is removed from the outer sleeve and as the tip cap is removed and disconnected from the discharge port of the syringe. Therefore, this retaining engagement feature of the indicator member on the tip cap is convenient to the user of the syringe, and further, provides a safety feature. In more specific terms, inadvertent failure to remove the indicator member from the syringe after the tip cap has been removed from the flow restricting engagement therewith, could possibly result in inadvertent disposition of the indicator member into the mouth of the patient.

In order to implement the aforementioned retaining engagement, at least one embodiment of the present invention includes a retaining structure mounted on and/or fixedly connected to the tip cap. Further, in at least one embodiment the retaining structure is fixedly connected to the flow restrictor of the tip cap. Also, the flow restrictor may include, but is not limited to, a flow restricting member in the form of a male plug, that is at least partially surrounded by a skirt, wherein the skirt is disposed radially outward from the male plug or other flow restrictor member in spaced relation thereto. In this embodiment, the retaining structure is connected to the surrounding skirt, preferably on an exterior thereof, in outwardly spaced relation to the male plug. Such an outwardly spaced disposition of the retaining structure and flow restrictor member, relative to the male plug, will help to eliminate interference with the discharge port of the syringe as it enters the interior of the outer sleeve in and an attempt to connect with the flow restrictor of the tip cap. It is emphasized that one embodiment of the flow restrictor is described as being a male plug type of flow restrictor. However structural and operative features of the present invention can be applied to a tip cap having a "female" flow restrictor with equal efficiency in terms of establishing and maintaining the aforementioned retaining engagement with the indicator member.

Additional structural features of one or more embodiments of the present invention include the retaining structure having at least one retaining member secured outwardly from the male plug of the flow restrictor, such as being connected to and extending outwardly from exterior surface of the surrounding skirt. Moreover, one or more additional embodiments of the present invention include the retaining structure comprising a plurality of retaining members each connected to an exterior surface of the surrounding skirt and extending radially outward therefrom in spaced relation to one another. Further, each of the one or more retaining members may be in the form of an elongated rib which is connected to and extends along at least a majority of the length and/or height of the flow restrictor.

Accordingly, in each of the aforementioned embodiments, the retaining structure and the flow restrictor to which it is attached are collectively structured to be disposed into and at least partially through an open interior of the indicator member, as the tip cap is being removed from the outer sleeve. Such concurrent removal of the tip cap and retained indicator member, from the outer sleeve, may typically occur after the syringe or other administering device is connected to the tip cap in the manner set forth herein. When so disposed in such an interior disposition, the retaining structure will establish the aforementioned retaining engagement with the indicator member. As indicated herein, the retaining engagement will be defined and/or established by the one or more retaining members establishing a frictional, interference fit with the interior surface of the substantially ring shaped indicator member. As further emphasized herein, such a frictional, interference fit will be sufficient to maintain retaining engagement of the indicator member on the tip cap as the tip cap is removed from the outer sleeve and also as the tip cap is removed and/or disconnected from the discharge port of the syringe.

These and other objects, features and advantages of the present invention will become clearer when the drawings as well as the detailed description are taken into consideration.

BRIEF DESCRIPTION OF THE DRAWINGS

For a fuller understanding of the nature of the present invention, reference should be had to the following detailed description taken in connection with the accompanying drawings in which.

Like reference numerals refer to like parts throughout the several views of the drawings.

DETAILED DESCRIPTION OF THE PREFERRED EMBODIMENT

Figure 1:
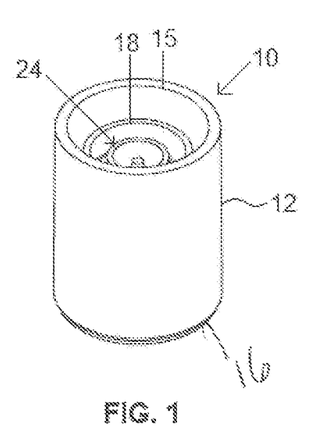
FIG. 1 is a perspective view of an assembled closure assembly of the present invention, including an outer sleeve and a tip cap removably contained therein.

With initial reference to FIG. 1, the present invention is directed to a closure assembly 10 for a medical administering device such as, but not limited to, a syringe (not shown). In addition, the closure assembly 10 of the present invention is specifically, but not exclusively, adapted for connection in "flow restricting engagement" with the discharge port of an oral syringe.

Figure 2:
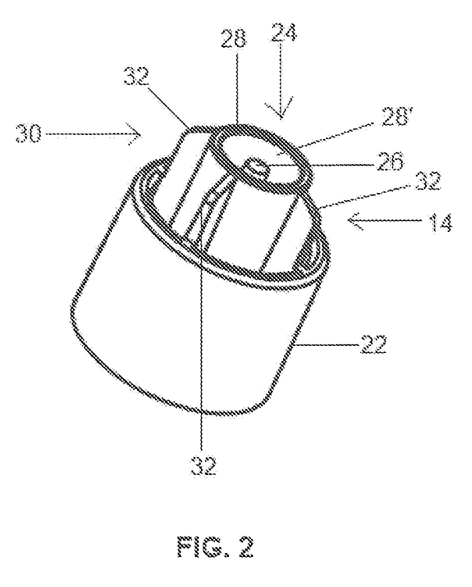
FIG. 2 is a perspective detail view of the tip cap of the closure assembly shown in the embodiment of FIG. 1.
Figure 3:
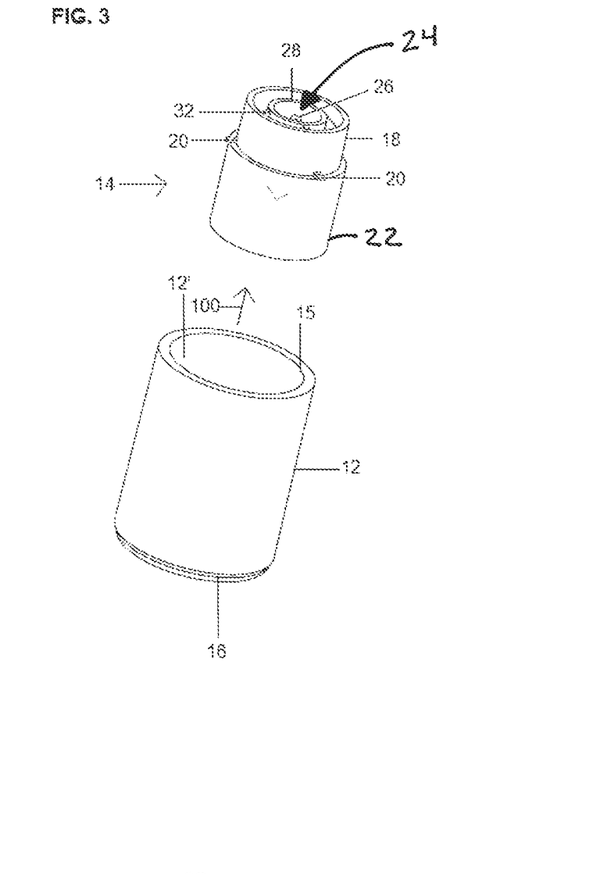
FIG. 3 is a perspective view in exploded form of the closure assembly of the embodiment of FIG. 1, wherein the tip cap of the embodiment of FIG. 2 is removed from the outer sleeve.
Figure 6:
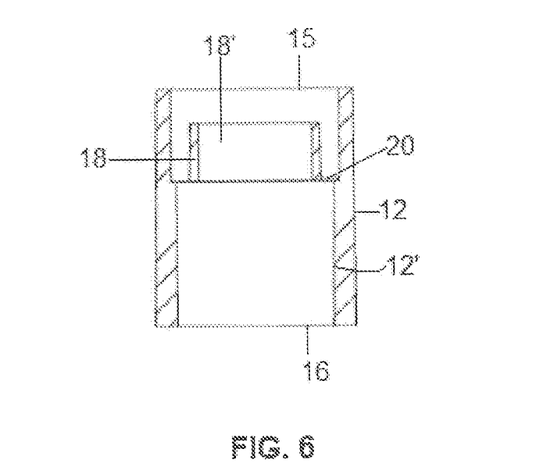
FIG. 6 is a longitudinal sectional view of the outer sleeve and indicator member, in assembled form.

As represented throughout the Figures, the closure assembly 10 includes an outer sleeve 12 and also, a tip cap 14 as perhaps best shown in FIGS. 2 and 3. The tip cap 14 is shown in detail in FIG. 2 and is represented in at least FIG. 4 as well, as being initially assembled on the interior of the outer sleeve 12 of the closure assembly 10. The outer sleeve 12 includes an access opening 15, which as illustrated in FIG. 1, may be disposed so as to define one open end of the outer sleeve 12, which also includes an oppositely disposed closed end 16. In addition, and as perhaps best shown in FIGS. 1, 3 and 6, the closure assembly 10 includes an indicator member 18 that is removably connected to one or more surface portions of the interior 12' of the outer sleeve 12. The removable interconnection of the indicator member 18 to and within the interior 12' of the outer sleeve 12 is accomplished by at least one, but preferably, a plurality of frangible members 20, as shown in FIG. 3. As also represented, the one or more frangible members 20 are disposed in removable interconnecting relation between an outer surface of the indicator member 18 and the surface of the interior 12' of the sleeve 12.

The tip cap 14 includes a base 22 and a flow restrictor generally indicated as 24. As represented in at least FIG. 3, the base 22 has a greater, outer transverse dimension than that of the indicator member 18. As a result, the interruptive disposition of the indicator member 18 relative to the tip cap 14 will result in the indicator member 18 being disconnected from the surface of the interior 12' of the outer sleeve 12, as the tip cap 14 is removed from the outer sleeve 12 through the access opening 15. Also, in at least one embodiment represented in the accompanying Figures, the flow restrictor 24 includes a restrictor member in the form of a male plug 26, that is structured to engage a female discharge port of a syringe, including an oral syringe, or other medical administering device. Further by way of example, the male plug 26 may be disposed within the interior of the female discharge port of the medical administering device, thereby establishing the aforementioned and intended flow restricting engagement therewith. While the embodiment in the accompanying figures represents the flow restrictor 24 as including the male "flow restricting" plug 26, it is emphasized that the flow restrictor 24 may take other configurations compatible with the configuration of the discharge port of the medical administering device, to which it is intended to be connected.

Further, in the embodiment represented in detail in FIG. 2, the flow restrictor 24 may include a skirt 28 disposed in outwardly spaced relation to the male plug 26 and preferably, but not necessarily, in surrounding relation thereto. As a result, an interior space 28' is defined and/or disposed within the skirt 28 and is specifically dimensioned and configured to receive the nozzle and/or other components of the discharge port of the syringe or administering device in a manner sufficient to establish a flow restricting engagement between the syringe discharge port and the male plug 26 of the flow restrictor 24.

As set forth herein, another inventive feature of the closure assembly 10 of the present invention is its ability to establish a fixed, retaining engagement between the tip cap 14, and more specifically, the flow restrictor 24, and the indicator member 18. Such retaining engagement will be maintained concurrent to the simultaneous removal of the tip cap 14 and indicator member 18 from the interior 12' of the outer sleeve 12, through the access opening 15. Accordingly, the closure assembly 10 and more specifically, the tip cap 14 of the present invention includes a retaining structure generally indicated as 30, connected thereto. The retaining structure 30 is disposed, dimensioned and configured to establish and maintain the aforementioned retaining engagement with the indicator member 18, as the tip cap 14 and indicator member 18 are concurrently removed from the interior 12' of the outer sleeve 12. Such removal is normally accomplished by the discharge port, nozzle or like structure of the syringe (or other administering device), passing through the access opening 15 into flow restricting connection with the flow restrictor 24 and male plug 26. Upon the establishment of this flow restricting connection, the syringe or other administering device may be removed from the outer sleeve 12 while the flow restrictor 24 is connected to the discharge port thereof.

Additional structural features of the retaining structure 30 include at least one retaining member 32 connected to and extending outwardly from the tip cap 14. However, in one or more preferred embodiments the retaining structure 30 includes a plurality of retaining members 32 each extending radially outward from the flow restrictor 24, in spaced relation to one another as clearly represented in FIG. 2. In at least one embodiment, the one or more retaining members 32 may be in the form of elongated or appropriately dimensioned ribs that are fixedly or integrally connected to the exterior surface of the skirt 28, as perhaps best illustrated in FIG. 2. This outward spacing assures the disposition of the one or more retaining members/ribs 32 in outwardly spaced relation to the restrictor member in the form of a male plug 26 of the flow restrictor 24. As a result, the interior spacing 28' between the skirt 28 and the flow restrictor in the form of male plug 26 is maintained for reception of the discharge port of the syringe (or other administering device) at least partially within the space 28' and into connection with the flow restrictor 24.

Figure 4:
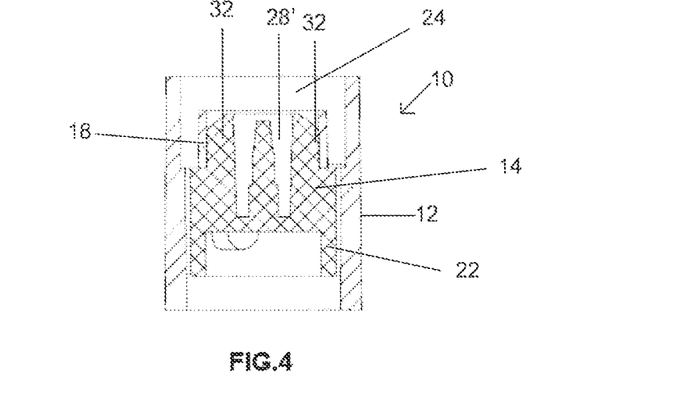
FIG. 4 is a longitudinal sectional view of the closure assembly of the embodiment of FIG. 1.
Figure 5:
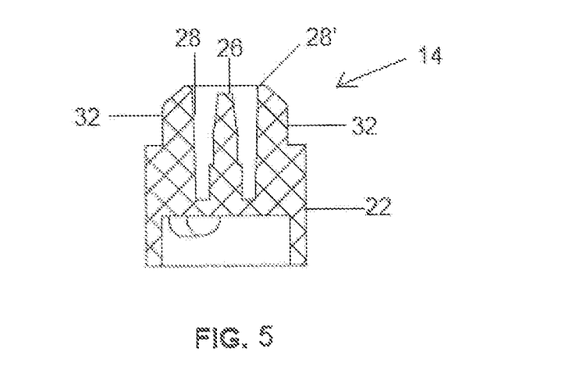
FIG. 5 is a longitudinal sectional view of the tip cap of the embodiment of FIG. 3.

As represented in FIGS. 1 and 4, when originally assembled, the tip cap 14 is disposed within the interior of the outer sleeve 12, with the indicator member 18 disposed above the aforementioned closed end 16 of the outer sleeve 12. In such an assembled position, the tip cap 14 is removably retained within the outer sleeve 12 due to the aforementioned removable attachment of the indicator member 18 to the surface of the interior 12' of the outer sleeve 12 by frangible "interconnecting" members 20. Because the indicator member 18 cannot be re-attached to the surface of the interior 12' of the outer sleeve 12, attempts to reposition the outer sleeve 12 in enclosing, retaining relation to the tip cap 14 will not be possible.

The aforementioned retaining engagement between the tip cap 14 and the indicator member 18 may be considered a fixed attachment, more specifically defined by a frictional, interference fit therebetween. Further, the retaining engagement of the indicator member 18 on the tip cap 14 will be maintained when they are simultaneously removed from the interior of the outer sleeve 12, as schematically represented in FIG. 3, by directional arrow 100. It is of further note that the retaining engagement between the indicator member 18 and the tip cap 14 will be maintained when the tip cap 14 and the retained indicator member 18 are concurrently removed from the discharge port of the syringe (not shown). As a result, when the syringe or administering device is used to administer the contents thereof to a patient, a user of the syringe will not be required to first remove the tip cap 14 and thereafter separately remove the indicator member 18 from the syringe, as is frequently required with known or prior art closure assemblies. Therefore, this retaining feature and/or retaining engagement of the indicator member 18 on the tip cap 14 is not only a matter of convenience to the user of the syringe, but also serves as a significant safety feature. In more specific terms, inadvertent failure to remove the indicator member 18 from the syringe after the tip cap 14 has been removed from the flow restricting engagement therewith, could possibly result in inadvertent disposition of the indicator member into the mouth or other body portion of the patient.

In order to efficiently implement the aforementioned retaining engagement, the retaining structure 30, including the one or more retaining members, in the illustrated embodiment having the form of a rib 32, is fixedly connected to the skirt 28 of the flow restrictor 24, in outwardly spaced relation to the restrictor member in the form of male plug 26, in aligned relation to the indicator member 18. As such, the retaining structure 30, including the one or more retaining members 32 are cooperatively disposed, dimensioned and structured with the indicator member 18 to efficiently and reliably establish and maintain the aforementioned retaining engagement therebetween, as represented in FIGS. 3 and 4. Such retaining engagement will be maintained when the tip cap 14 and indicator member 18 are simultaneously removed from the outer sleeve 12. More specifically, and as represented in at least FIGS. 4 and 6, the indicator member 18 is disposed in interruptive relation to passage of the tip cap 14 through the access opening 15, such as when it is connected to a discharge port of the syringe or other medical administering device. In at least one embodiment, further cooperative structuring between the indicator member 18 and the tip cap 14 comprises the indicator member 18 including an open interior 18'. In addition, the indicator member 18 may be structured in the form of a ring or to otherwise include a substantially annular configuration at least partially defining the open interior 18'.

To further establish and maintain the aforementioned retaining engagement between the indicator member 18 and the tip cap 14, the retaining member 30, including one or more retaining members 32 are cooperatively dimensioned to pass and/or be positioned within the open interior 18' of the indicator member 18, as clearly represented in FIGS. 3 and 4. The outside dimensioning of the one or more retaining members 32 and the interior 18' of the indicator member 18 are substantially equal and or minimally different to establish the interior disposition of the retaining structure 30 and the aforementioned frictional, interference fit therebetween. Accordingly, retaining engagement as represented in FIGS. 3 and 4 of the indicator member 18 on the tip cap 14 is defined by the frictional, interference fit of the one or more retaining members 32 within the open interior 18' of the indicator member 18.

Since many modifications, variations and changes in detail can be made to the described preferred embodiment of the invention, it is intended that all matters in the foregoing description and shown in the accompanying drawings be interpreted as illustrative and not in a limiting sense. Thus, the scope of the invention should be determined by the appended claims and their legal equivalents.

What is claimed is:

1. A closure assembly for a medical administering device comprising:

an outer sleeve including an access opening;

a tip cap including a flow restrictor, said tip cap disposed within said outer sleeve, said tip cap structured for removable, flow restricting connection to a discharge port of the medical administering device, an indicator member removably connected to and within said outer sleeve, between said tip cap and said access opening, in interruptive relation to said tip cap, a retaining structure disposed in interconnecting relation between said indicator member and said flow restrictor, said retaining structure and said flow restrictor being collectively dimensioned to pass interiorly of said indicator member into a retaining engagement with said indicator member, said retaining structure comprising at least one retaining member comprising an elongated rib fixedly connected to an exterior of said flow restrictor along at least a majority of a length thereof,
said elongated rib extending outwardly from said flow restrictor in said retaining engagement with an interior of said indicator member, concurrent to said interconnecting relation between said indicator member and said flow restrictor,
said retaining engagement of said elongated rib with said interior of said indicator member comprising a frictional, interference fit therebetween,
wherein said tip cap and said indicator member are cooperatively structured to define said retaining engagement therebetween, concurrent to connection of said tip cap to the medical administering device and removal of said tip cap and the medical administering device from said outer sleeve.

2. A closure assembly as recited in claim 1, wherein said retaining engagement comprises said indicator member fixedly attached to said tip cap, concurrent to removal of said tip cap from said flow restricting connection with the medical administering device.

3. The closure assembly as recited in claim 1, wherein said retaining engagement further comprises said flow restrictor disposed interiorly of said indicator member in interconnected relation thereto.

4. The closure assembly as recited in claim 3, wherein said indicator member comprises a ring including an open interior, said retaining engagement further comprising said flow restrictor being disposed interiorly of said ring, within said open interior, in interconnected relation to said ring.

5. The closure assembly as recited in claim 1, wherein said retaining structure is fixedly attached to said flow restrictor and movable therewith relative to said outer sleeve.

6. The closure assembly as recited in claim 1, wherein said retaining structure comprises a plurality of retaining members each fixedly connected to said flow restrictor and extending outwardly therefrom in retaining engagement with said interior of said indicator member, concurrent to said interconnecting relation between said indicator member and said flow restrictor.

7. The closure assembly as recited in claim 6, wherein said retaining engagement of said plurality of retaining members with said interior of said indicator member comprises a frictional, interference fit therebetween.

8. The closure assembly as recited in claim 6, wherein each of said plurality of retaining members comprise an elongated rib connected to an exterior of said flow restrictor and extending along at least a majority of a length thereof.

9. The closure assembly as recited in claim 8, wherein each of said plurality of ribs includes an outer peripheral edge; and said interconnecting relation between said indicator member and said flow restrictor comprises a frictional, interference fit of each of said peripheral edges with said interior of said indicator member.

10. A closure assembly for a medical administering device comprising:
an outer sleeve including an access opening,
a tip cap removably disposed within said outer sleeve and including a flow restrictor, said flow restrictor structured for removable, flow restricting connection to a discharge port of the administering device,
an indicator member removably connected to and within said outer sleeve, in interruptive relation to passage of said tip cap through said access opening,
a retaining structure fixedly connected to said flow restrictor and movable therewith relative to said indicator member,
said retaining structure and said flow restrictor collectively dimensioned and structured for a retaining engagement thereof with said indicator member, concurrent to attachment of said tip cap to the medical administering device and removal thereof from said outer sleeve,
said retaining structure and said flow restrictor being cooperatively dimensioned and structured to collectively pass into an interior of said indicator member into said retaining engagement,
said retaining engagement further comprising said indicator member fixedly attached to and said tip cap, concurrent to removal of said tip cap from said flow restricting connection with the medical administering device, and
said retaining structure comprising a plurality of retaining members defined by a plurality of elongated ribs extending along at least a majority of a length of said flow restrictor, said plurality of elongated ribs connected to an exterior of said flow restrictor in spaced relation to one another and extending radially outwardly therefrom.

11. The closure assembly as recited in claim 10, wherein said retaining engagement is at least partially defined by a fixed, frictional, interference fit between said plurality of elongated ribs and said interior of said indicator member.

12. A closure assembly for a medical administering device comprising:
an outer sleeve including an access opening;
a tip cap including a flow restrictor, said tip cap disposed within said outer sleeve,
said tip cap structured for removable, flow restricting connection to a discharge port of the medical administering device,
an indicator member removably connected to and within said outer sleeve, between said tip cap and said access opening, in interruptive relation to said tip cap, a retaining structure disposed in interconnecting relation between said indicator member and said flow restrictor,
said retaining structure and said flow restrictor being collectively dimensioned to pass interiorly of said indicator member into said retaining engagement with said indicator member,
said retaining structure comprising a plurality of retaining members each defined by an elongated rib extending along at least a majority of a length of said flow restrictor, said plurality of elongated ribs fixedly connected to an exterior of said flow restrictor in spaced relation to one another and extending radially outwardly therefrom,
wherein said tip cap and said indicator member are cooperatively structured to define a retaining engagement therebetween, concurrent to connection of said tip cap to the medical administering device and removal of said tip cap and the medical administering device from said outer sleeve.

\* \* \* \* \*